US00RE42016E

(19) United States
(12) Reissued Patent
Chornenky et al.

(10) Patent Number: US RE42,016 E
(45) Date of Reissued Patent: Dec. 28, 2010

(54) APPARATUS AND METHOD FOR THE TREATMENT OF BENIGN PROSTATIC HYPERPLASIA

(75) Inventors: Victor I. Chornenky, Minnetonka, MN (US); Ali Jaafar, Eden Prairie, MN (US)

(73) Assignee: AngioDynamics, Inc., Latham, NY (US)

(21) Appl. No.: 12/572,047

(22) Filed: Oct. 1, 2009

Related U.S. Patent Documents

Reissue of:
(64) Patent No.: 7,130,697
Issued: Oct. 31, 2006
Appl. No.: 10/668,775
Filed: Sep. 23, 2003

U.S. Applications:
(63) Continuation-in-part of application No. 10/217,749, filed on Aug. 13, 2002, now Pat. No. 6,994,706.
(60) Provisional application No. 60/412,705, filed on Sep. 23, 2002, provisional application No. 60/325,994, filed on Oct. 1, 2001, and provisional application No. 60/311,792, filed on Aug. 13, 2001.

(51) Int. Cl.
*A61F 2/00* (2006.01)
*A61B 18/18* (2006.01)

(52) U.S. Cl. ..... 607/101; 606/41; 607/116
(58) Field of Classification Search ..... 606/27–31, 606/41, 47–50; 607/101, 102, 115, 116, 143; 604/22
See application file for complete search history.

(56) References Cited

U.S. PATENT DOCUMENTS

| | | | |
|---|---|---|---|
| 1,653,819 | A | 12/1927 | Northcott et al. |
| 4,016,886 | A | 4/1977 | Doss |
| 4,226,246 | A | 10/1980 | Fragnet |
| 4,262,672 | A | 4/1981 | Kief |

(Continued)

FOREIGN PATENT DOCUMENTS

| | | |
|---|---|---|
| DE | 863111 | 1/1953 |

(Continued)

OTHER PUBLICATIONS

Amasha, et al., Quantitative Assessment of Impedance Tomography for Temperature Measurements in Microwave Hyperthermia, *Clin. Phys. Physiol. Meas.*, 1998, Suppl. A, 49–53.

(Continued)

*Primary Examiner*—Michael Peffley
(74) *Attorney, Agent, or Firm*—Harry K. Ahn; Abelman Frayne & Schwab

(57) ABSTRACT

An apparatus and method for treatment of benign prostatic hyperplasia is disclosed wherein the apparatus includes an applicator having a probe having proximal and distal probe sections wherein the proximal and distal probe sections each define an axis and wherein the axes are not collinear.

16 Claims, 2 Drawing Sheets

U.S. PATENT DOCUMENTS 4,407,943 A 10/1983 Cole et al.
4,810,963 A 3/1989 Blake-Coleman et al.
4,907,601 A 3/1990 Frick
4,946,793 A 8/1990 Marshall, III
5,019,034 A 5/1991 Weaver et al.
5,052,391 A 10/1991 Silberstone et al.
5,058,605 A 10/1991 Slovak
5,098,843 A 3/1992 Calvin
5,134,070 A 7/1992 Casnig
5,173,158 A 12/1992 Schmukler
5,193,537 A 3/1993 Freeman
5,273,525 A 12/1993 Hofmann
5,283,194 A 2/1994 Schmukler
5,318,563 A 6/1994 Malis et al.
5,328,451 A 7/1994 Davis et al.
5,389,069 A 2/1995 Weaver
5,403,311 A 4/1995 Abele et al.
5,425,752 A 6/1995 Vu'Nguyen
5,439,440 A 8/1995 Hofmann
5,458,625 A 10/1995 Kendall
5,533,999 A 7/1996 Hood et al.
5,536,240 A 7/1996 Edwards et al.
5,575,811 A 11/1996 Reid et al.
5,626,146 A 5/1997 Barber et al.
5,634,899 A 6/1997 Shapland et al.
5,674,267 A 10/1997 Mir et al.
5,702,359 A 12/1997 Hofmann
5,720,921 A 2/1998 Meserol
5,778,894 A 7/1998 Dorogi et al.
5,782,882 A 7/1998 Lerman et al.
5,800,378 A 9/1998 Edwards et al.
5,810,762 A 9/1998 Hofmann
5,836,905 A 11/1998 Lemelson et al.
5,843,026 A * 12/1998 Edwards et al. ..... 604/508
5,873,849 A 2/1999 Bernard
5,919,142 A 7/1999 Boone et al.
5,947,889 A 9/1999 Hehrlein
5,983,131 A 11/1999 Weaver et al.
5,991,697 A 11/1999 Nelson et al.
5,999,847 A 12/1999 Elstrom
6,009,347 A 12/1999 Hofmann
6,010,613 A 1/2000 Walters et al.
6,016,452 A 1/2000 Kasevich
6,041,252 A 3/2000 Walker et al.
6,055,453 A 4/2000 Hofmann et al.
6,068,650 A 5/2000 Nanda et al.
6,085,115 A 7/2000 Weaver et al.
6,090,106 A 7/2000 Goble et al.
6,102,885 A 8/2000 Bass
6,106,521 A 8/2000 Blewett et al.
6,109,270 A 8/2000 Mah et al.
6,122,599 A 9/2000 Mehta
6,132,419 A 10/2000 Hofmann
6,159,163 A 12/2000 Strauss et al.
6,208,893 B1 * 3/2001 Hofmann ..... 604/21
6,210,402 B1 4/2001 Olsen et al.
6,212,433 B1 4/2001 Behl
6,216,034 B1 4/2001 Hofmann
6,219,577 B1 4/2001 Brown et al.
6,241,702 B1 6/2001 Lundquist et al.
6,261,831 B1 7/2001 Agee
6,278,895 B1 8/2001 Bernard
6,300,108 B1 10/2001 Rubinsky
6,326,177 B1 12/2001 Schoenbach et al.
6,347,247 B1 2/2002 Dev et al.
6,349,233 B1 2/2002 Adams
6,351,674 B2 2/2002 Silverstone
6,387,671 B1 5/2002 Rubinsky et al.
6,403,348 B1 6/2002 Rubinsky et al.
6,470,211 B1 10/2002 Ideker et al.
6,482,619 B1 11/2002 Rubinsky et al.
6,493,592 B1 12/2002 Leonard et al.
6,500,173 B2 12/2002 Underwood et al.
6,526,320 B2 2/2003 Mitchell
6,562,604 B2 5/2003 Rubinsky et al.
6,607,529 B1 * 8/2003 Jones et al. ..... 606/47
6,611,706 B2 8/2003 Avrahami et al.
6,613,211 B1 9/2003 McCormick et al.
6,627,421 B1 9/2003 Unger et al.
6,653,091 B1 11/2003 Dunn et al.
6,669,691 B1 12/2003 Taimisto
6,692,493 B2 * 2/2004 McGovern et al. ..... 606/41
6,697,669 B2 2/2004 Dev et al.
6,697,670 B2 2/2004 Chornenky et al.
6,702,808 B1 3/2004 Kreindel
6,795,728 B2 9/2004 Chornenky et al.
6,801,804 B2 10/2004 Miller et al.
6,865,416 B2 3/2005 Dev et al.
6,892,099 B2 5/2005 Jaafar et al.
6,912,417 B1 6/2005 Bernard et al.
6,927,049 B2 8/2005 Rubinsky et al.
6,962,587 B2 11/2005 Johnson et al.
6,972,014 B2 12/2005 Eum et al.
6,994,706 B2 2/2006 Chornenky et al.
7,053,063 B2 5/2006 Rubinsky et al.
7,063,698 B2 6/2006 Whayne et al.
7,130,697 B2 10/2006 Chornenky et al.
7,211,083 B2 5/2007 Chornenky et al.
7,267,676 B2 9/2007 Chornenky et al.
2001/0044596 A1 11/2001 Jaafar
2002/0010491 A1 1/2002 Schoenbach
2002/0055731 A1 5/2002 Atala et al.
2002/0077676 A1 6/2002 Schroeppel et al.
2002/0099323 A1 7/2002 Dev et al.
2002/0138117 A1 9/2002 Son
2002/0193831 A1 12/2002 Smith, III
2003/0009110 A1 1/2003 Tu et al.
2003/0060856 A1 3/2003 Chornenky et al.
2003/0088199 A1 5/2003 Tu et al.
2003/0130711 A1 7/2003 Pearson et al.
2003/0170898 A1 9/2003 Gundersen et al.
2003/0208200 A1 11/2003 Palanker et al.
2003/0225360 A1 12/2003 Eppstein et al.
2004/0019371 A1 1/2004 Jaafar et al.
2004/0059389 A1 3/2004 Chornenky et al.
2004/0146877 A1 7/2004 Diss et al.
2004/0153057 A1 8/2004 Davison
2004/0243107 A1 12/2004 Mackoviak
2004/0267189 A1 12/2004 Mavor et al.
2005/0043726 A1 2/2005 McHale et al.
2005/0049541 A1 3/2005 Behar et al.
2005/0165393 A1 7/2005 Eppstein
2005/0171523 A1 8/2005 Rubinsky et al.
2005/0171574 A1 8/2005 Rubinsky et al.
2005/0182462 A1 8/2005 Chornenky et al.
2005/0261672 A1 11/2005 Deem et al.
2005/0288730 A1 12/2005 Deem et al.
2006/0015147 A1 1/2006 Persson et al.
2006/0025760 A1 2/2006 Podhajsky
2006/0079883 A1 * 4/2006 Elmouelhi et al. ..... 606/41
2006/0121610 A1 6/2006 Rubinsky et al.
2006/0212078 A1 9/2006 Demarais et al.
2006/0217703 A1 9/2006 Chornenky et al.
2006/0264752 A1 11/2006 Rubinsky et al.
2007/0043345 A1 2/2007 Davalos et al.
2007/0118069 A1 5/2007 Persson et al.
2008/0052786 A1 2/2008 Lin et al.

FOREIGN PATENT DOCUMENTS

DE 4000893 7/1991
EP 0378132 7/1990

| | | |
|---|---|---|
| EP | 0935482 | 5/2005 |
| WO | 9639531 | 12/1996 |
| WO | 0020554 | 4/2000 |
| WO | 0107583 | 2/2001 |
| WO | 0107584 | 2/2001 |
| WO | 0107585 | 2/2001 |
| WO | 0181533 | 11/2001 |
| WO | 2004037341 | 5/2004 |

OTHER PUBLICATIONS

Andreason, Electroporation as a Technique for the Transfer of Macromolecules into Mammalian Cell Lines, *J. Tiss. Cult. Meth.,* 15:56–62, 1993.

Baker, et al., Calcium–Dependent Exocytosis in Bovine Adrenal Medullary Cells with Leaky Plasma Membranes, *Nature,* vol. 276, pp. 620–622, 1978.

Barber, Electrical Impedance Tomography Applied Potential Tomography, Advances in Biomedical Engineering, Beneken and Thevenin, eds., IOS Press, 1993.

Beebe, S.J., et al., Nanosecond pulsed electric field (nsPEF) effects on cells and tissues: apoptosis induction and tumor growth inhibition. PPPS–2001 Pulsed Power Plasma Science 2001, 28$^{th}$ IEEE International Conference on Plasma Science and 13$^{th}$ IEEE International Pulsed Power Conference, Digest of Technical Papers (Cat. No. 01CH37251). IEEE, Part vol. 1, 2001, pp. 211–215, vol. I, Piscataway, NJ, USA.

Blad, et al., Impedance Spectra of Tumour Tissue in Comparison with Normal Tissue; a Possible Clinical Application for Electrical Impedance Tomography, *Physiol. Meas.* 17 (1996) A105–A115.

Bown, S.G., Phototherapy of tumors. *World J. Surgery,* 1983. 7: p. 700–9.

BPH Management Strategies: Improving Patient Satisfaction, *Urology Times,* May 2001, vol. 29, Supplement 1.

Brown, et al., Blood Flow Imaging Using Electrical Impedance Tomography, *Clin. Phys. Physiol. Meas.,* 1992, vol. 13, Suppl. A, 175–179.

Chandrasekar, et al., Transurethral Needle Ablation of the Prostate (TUNA)—a Propsective Study, Six Year Follow Up, (Abstract), Presented at 2001 National Meeting, Anaheim, CA, Jun. 5, 2001.

Coates, C.W.,et al., "The Electrical Discharge of the Electric Eel, Electrophorous Electricus," Zoologica, 1937, 22(1), pp. 1–32.

Cook, et al., ACT3: A High–Speed, High–Precision Electrical Impedance Tomograph, *IEEE Transactions on Biomedical Engineering,* vol. 41, No. 8, Aug. 1994.

Cowley, Good News for Boomers, *Newsweek,* Dec. 30, 1996/Jan. 6, 1997.

Cox, et al., Surgical Treatment of Atrial Fibrillation: A Review, *Europace* (2004) 5, S20–S–29.

Crowley, Electrical Breakdown of Biomolecular Lipid Membranes as an Electromechanical Instability, *Biophysical Journal,* vol. 13, pp. 711–724, 1973.

Davalos, et al., Tissue Ablation with Irreversible Electroporation, *Annals of Biomedical Engineering,* vol. 33, No. 2, Feb. 2005.

Davalos, et al., Theoretical Analysis of the Thermal Effects During In Vivo Tissue Electroporation, Bioelectrochemistry, vol. 61, pp. 99–107, 2003.

Davalos, et al., A Feasibility Study for Electrical Impedance Tomography as a Means to Monitor T issue Electroporation for Molecular Medicine, *IEEE Transactions on Biomedical Engineering,* vol. 49, No. 4, Apr. 2002.

Davalos, Real–Time Imaging for Molecular Medicine through Electrical Impedance Tomography of Electroporation, Dissertation for Ph.D. in Engineering–Mechanical Engineering, Graduate Division of University of California, Berkeley, 2002.

Dean, Nonviral Gene Transfer to Skeletal, Smooth, and Cardiac Muscle in Living Animals, *Am J. Physiol Cell Physiol* 289: 233–245, 2005.

Dev, et al., Sustained Local Delivery of Heparin to the Rabbit Arterial Wall with an Electroporation Catheter, *Catheterization and Cardiovascular Diagnosis,* Nov. 1998, vol. 45, No. 3, pp. 337–343.

Dev, et al., Medical Applications of Electroporation, *IEEE Transactions of Plasma Science,* vol. 28, No. 1, pp. 206–223, Feb. 2000.

Duraiswami, et al., Boundary Element Techniques for Efficient 2–D and 3–D Electrical Impedance Tomography, *Chemical Engineering Science,* vol. 52, No. 13, pp. 2185–2196, 1997.

Duraiswami, et al., Efficient 2D and 3D Electrical Impedance Tomography Using Dual Reciprocity Boundary Element Techniques, *Engineering Analysis with Boundary Elements*22, (1998) 13–31.

Duraiswami, et al., Solution of Electrical Impedance Tomography Equations Using Boundary Element Methods, *Boundary Element Technology* XII, 1997, pp. 226–237.

Edd, J., et al., In–Vivo Results of a New Focal Tissue Ablation Technique: Irreversible Electroporation, *IEEE Trans. Biomed. Eng.* 53 (2006) p. 1409–1415.

Erez, et al., Controlled Destruction and Temperature Distributions in Biological Tissues Subjected to Monoactive Electrocoagulation, *Transactions of the ASME: Journal of Mechanical Design,* vol. 102, Feb. 1980.

Foster, R.S., et al., High–intensity focused ultrasound in the treatment of prostactic disease. *Eur. Urol.,* 1993. 23: 44–7).

Fox, et al., Sampling Conductivity Images via MCMC, Mathematics Department, Auckland University, New Zealand, May 1997.

Gauger, et al., A Study of Dielectric Membrane Breakdown in the Fucus Egg, *J. Membrane Biol.,* vol. 48, No. 3, pp. 249–264, 1979.

Gehl, et al., In Vivo Electroporation of Skeletal Muscle: Threshold, Efficacy and Relation to Electric Field Distribution, *Biochimica et Biphysica Acta* 1428, 1999, pp. 233–240.

Gençer, et al., Electrical Impedance Tomography: Induced–Current Imaging Achieved with a Multiple Coil System, *IEEE Transactions on Biomedical Engineering,* vol. 43, No. 2, Feb. 1996.

Gilbert, et al., Novel Electrode Designs for Electrochemotheraphy, *Biochimica et Biophysica Acta* 1334, 1997, pp. 9–14.

Gilbert, et al., The Use of Ultrasound Imaging for Monitoring Cryosurgery, Proceedings 6$^{th}$ Annual Conference, IEEE Engineering in Medicine and Biology, 107–111, 1984.

Glidewell, et al., The Use of Magnetic Resonance Imaging Data and the Inclusion of Anisotropic Regions in Electrical Impedance Tomography, *Biomed, Sci. Instrum.* 1993; 29: 251–7.

Gothelf, et al., Electrochemotherapy: Results of Cancer Treatment Using Enhanced Delivery of Bleomycin by Electroporation, *Cancer Treatment Reviews* 2003: 29: 371–387.

Griffiths, et al., A Dual–Frequency Electrical Impedance Tomography System, *Phys. Med. Biol.,* 1989, vol. 34, No. 10, pp. 1465–1476.

Griffiths, The Importance of Phase Measurement in Electrical Impedance Tomography, *Phys. Med. Biol.,* 1987, vol. 32, No. 11, pp. 1435–1444.

Griffiths, Tissue Spectroscopy with Electrical Impedance Tomography: Computer Simulations, *IEEE Transactions on Biomedical Engineering,* vol. 42, No. 9, Sep. 1995.

Gumerov, et al., The Dipole Approximation Method and Its Coupling with the Regular Boundary Element Method for Efficient Electrical Impedance Tomography, *Boundary Element Technology* XIII, 1999.

Hapala, Breaking the Barrier: Methods for Reversible Permeabilization of Cellular Membranes, *Critical Reviews in Biotechnology,* 17(2): 105–122, 1997.

Heller, et al., Clinical Applications of Electrochemotherapy, *Advanced Drug Delivery Reviews,* vol. 35, pp. 119–129, 1999.

Ho, et al., Electroporation of Cell Membranes: A Review, *Critical Reviews in Biotechnology,* 16(4): 349–362, 1996.

Holder, et al., Assessment and Calibration of a Low–Frequency System for Electrical Impedance Tomography (EIT), Optimized for Use in Imaging Brain Function in Ambulant Human Subjects, *Annals of the New York Academy of Science,* vol. 873, Issue 1, Electrical BI, pp. 512–519, 1999.

Huang, et al., Micro–Electroporation: Improving the Efficiency and Understanding of Electrical Permeabilization of Cells, *Biomedical Microdevices,* vol. 2, pp. 145–150, 1999.

Hughes, et al., An Analysis of Studies Comparing Electrical Impedance Tomography with X–Ray Videofluoroscopy in the Assessment of Swallowing, *Physiol. Meas.* 15, 1994, pp. A199–A209.

Issa, et al., The TUNA Procedure for BPH: Review of the Technology: The TUNA Procedure for BPH: Basic Procedure and Clinical Results, Reprinted from *Infections in Urology,* Jul./Aug. 1998 and Sep./Oct. 1998.

Ivanuša, et al., MRI Macromolecular Contrast Agents as Indicators of Changed Tumor Blood Flow, *Radiol. Oncol.* 2001; 35(2): 139–47.

Jaroszeski, et al., In Vivo Gene Delivery by Electroporation, *Advanced Drug Delivery Review,* vol. 35, pp. 131–137, 1999.

Kinosita, et al., Hemolysis of Human Erythrocytes by a Transient Electric Field, *Proc. Natl. Acad. Sci. USA,* vol. 74, No. 5, pp. 1923–1927, 1977.

Liu, et al., Measurement of Pharyngeal Transit Time by Electrical Impedance Tomography, *Clin. Phys. Physiol. Meas.,* 1992, vol. 13, Suppl. A, pp. 197–200.

Lundqvist, et al., Altering the Biochemical State of Individual Cultured Cells and Organelles with Ultramicroelectrodes, *Proc. Natl. Acad. Sci. USA,* vol. 95, pp. 10356–10360, Sep. 1998.

Lurquin, Gene Transfer by Electroporation, *Molecular Biotechnology,* vol. 7, 1997.

Lynn, et al., A New Method for the Generation and Use of Focused Ultrasound in Experimental Biology, *The Journal of General Physiology,* vol. 26, 179–193, 1942.

Miklavčič, et al., A Validated Model of an in Vivo Electric Field Distribution in Tissues for Electrochemotherapy and for DNA Electrotransfer for Gene Therapy, *Biochimica et Biophysica Acta* 1523 (2000), pp. 73–83.

Miklavčič, et al., The Importance of Electric Field Distribution for Effective in Vivo Electroporation of Tissues, *Biophysical Journal,* vol. 74, May 1998, pp. 2152–2158.

Miller, L., et al., Cancer cells ablation with irreversible electroporation, *Technology in Cancer Research and Treatment* 4 (2005) 699–706.

Mir, Therapeutic Perspectives of In Vivo Cell Electropermeabilization, *Bioelectrochemistry,* vol. 53, pp. 1–10, 2000.

Mir, L.M., et al., Electric Pulse–Mediated Gene Delivery to Various Animal Tissues, in Advances in Genetics, Academic Press, 2005, p. 83–114.

Mir, L.M. and Orlowski, S., The basis of electrochemotherapy, in Electrochemotherapy, electrogenetherapy, and transdermal drug delivery: electrically mediated delivery of molecules to cells, M.J. Jaroszeski, R. Heller, R. Gilbert, Editors, 2000, Humana Press, p. 99–118.

Mir, et al., Effective Treatment of Cutaneous and Subcutaneous Malignant Tumours by Electrochemotherapy, *British Journal of Cancer,* vol. 77, No. 12, pp. 2336–2342, 1998.

Mir, et al., Electrochemotherapy Potentiation of Antitumour Effect of Bleomycin by Local Electric Pulses, *European Journal of Cancer,* vol. 27, No. 1, pp. 68–72, 1991.

Mir, et al., Electrochemotherapy, a Novel Antitumor Treatment: First Clinical Trial, *C.R. Acad. Sci. Paris,* Ser. III, vol. 313, pp. 613–618, 1991.

Narayan, et al., Establishment and Characterization of a Human Primary Prostatic Adenocarcinoma Cell Line (ND–1), *The Journal of Urology,* vol. 148, 1600–1604, Nov. 1992.

Naslund, Michael J., Transurethral Needle Ablation of the Prostate, *Urology,* vol. 50, No. 2, Aug. 1997.

Naslund, Cost–Effectiveness of Minimally Invasive Treatments and Transurethral Resection (TURP) in Benign Prostatic Hyperplasia (BPH), (Abstract), Presented at 2001 AUA National Meeting,, Anaheim, CA, Jun. 5, 2001.

Neumann, et al., Gene Transfer into Mouse Lyoma Cells by Electroporation in High Electric Fields, *J. Embo.,* vol. 1, No. 7, pp. 841–845, 1982.

Neumann, et al., Permeability Changes Induced by Electric Impulses in Vesicular Membranes, *J. Membrane Biol.,* vol. 10, pp. 279–290, 1972.

Okino, et al., Effects of High–Voltage Electrical Impulse and an Anticancer Drug on In Vivo Growing Tumors, *Japanese Journal of Cancer Research,* vol. 78, pp. 1319–1321, 1987.

Onik, et al., Sonographic Monitoring of Hepatic Cryosurgery in an Experimental Animal Model, *AJR American J. of Roentgenology,* vol. 144, pp. 1043–1047, May 1985.

Onik, et al., Ultrasonic Characteristics of Frozen Liver, *Cryobiology,* vol. 21, pp. 321–328, 1984.

Organ, L.W., Electrophysiological principles of radiofrequency lesion making, *Apply. Neurophysiol.,*1976. 39: p. 69–76.

Piñero, et al., Apoptotic and Necrotic Cell Death Are Both Induced by Electroporation in HL60 Human Promyeloid Leukaemia Cells, *Apoptosis,* vol. 2, No. 3, 330–336, Aug. 1997.

Rols, M.P., et al., Highly Efficient Transfection of Mammalian Cells by Electric Field Pulses: Application to Large Volumes of Cell Culture by Using a Flow System, *Eur. J. Biochem.* 1992, 206, pp. 115–121.

Rubinsky, B., ed, Cryosurgery. *Annu Rev. Biomed.* Eng. vol. 2 2000. 157–187.

Sersa, et al., Reduced Blood Flow and Oxygenation in SA–1 Tumours after Electrochemotherapy with Cisplatin, *British Journal of Cancer,* 87, 1047–1054, 2002.

Sersa, et al., Tumour Blood Flow Modifying Effects of Electrochemotherapy: a Potential Vascular Targeted Mechanism, *Radiol. Oncol.,* 37(1): 43–8, 2003.

Sharma, et al., Poloxamer 188 Decreases Susceptibility of Artificial Lipid Membranes to Electroporation, *Biophysical Journal,* vol. 71, No. 6, pp. 3229–3241, Dec. 1996.

Shiina, S., et al, Percutaneous ethanol injection therapy for hepatocellular carcinoma: results in 146 patients. *AJR,* 1993, 160: p. 1023–8.

Thompson, et al., To determine whether the temperature of 2% lignocaine gel affects the initial discomfort which may be associated with its instillation into the male urethra, *BJU International* (1999), 84, 1035–1037.

Weaver, Electroporation: A General Phenomenon for Manipulating Cells and Tissues, *Journal of Cellular Biochemistry,* 51: 426–435, 1993.

Weaver, et al., Theory of Electroporation: A Review, *Bioelectrochemistry and Bioenergetics,* vol. 41, pp. 136–160, 1996.

Zimmermann, et al., Dielectric Breakdown of Cell Membranes, *Biophysical Journal,* vol. 14, No. 11, pp. 881–899, 1974.

Zlotta, et al., Possible Mechanisms of Action of Transurethral Needle Ablation of the Prostate on Benign Prostatic Hyperplasia Symptoms: a Neurohistochemical Study, Reprinted from *Journal of Urology,* vol. 157, No. 3, Mar. 1997, pp. 894–899.

Zlotta, et al., Long–Term Evaluation of Transurethral Needle Ablation of the Prostate (TUNA) for Treatment of Benign Prostatic Hyperplasia (BPH): Clinical Outcome After 5 Years. (Abstract) Presented at 2001 AUA National Meeting, Anaheim, CA—Jun. 5, 2001.

* cited by examiner

APPARATUS AND METHOD FOR THE TREATMENT OF BENIGN PROSTATIC HYPERPLASIA

Matter enclosed in heavy brackets [ ] appears in the original patent but forms no part of this reissue specification; matter printed in italics indicates the additions made by reissue.

*CROSS-REFERENCE TO RELATED APPLICATIONS*

The present application claims priority to U.S. Provisional Application No. 60/412,705 entitled "Apparatus and method for treatment of benign prostatic hyperplasia by electroporation", which was filed Sep. 23, 2002. This application is a continuation-in-part of U.S. patent application Ser. No. 10/217,749 entitled "Apparatus and method for treatment of benign prostatic hyperplasia by electroporation", which was filed Aug. 13, 2002 (U.S. Patent Application Publication 2003/0060856, published Mar. 27, 2003) now U.S. Pat. No. 6,994,706, *which claims the benefit of U.S. Provisional Application Ser. No. 60/325,994 filed Oct. 1, 2001 and U.S. Provisional Application Ser. No. 60/311,792, filed Aug. 13, 2001.*

BACKGROUND OF THE INVENTION

1. Field of the Invention

The present invention relates generally to methods and apparatus for the electroporation of tissues and more specifically to such methods and apparatus for the treatment of benign prostatic hyperplasia.

2. Description of the Related Art

Though greater detail will follow in the discussion below, succinctly stated, the present invention provides apparatus and methods of providing treatment for the undesirable proliferation of cells in the prostate by killing the cells with electric field pulses of selected duration and strength to take advantage of a cellular event known as "electroporation."

Electroporation

The biophysical phenomenon known as electroporation refers to the use of electric field pulses to induce microscopic pores—"electropores"—in the lipid cell membranes. Depending on the parameters of the electric pulses, an electroporated cell can survive the pulsing or die. The cause of death of an electroporated cell is believed to be a chemical imbalance in the cell, resulting from the fluid communication with the extra-cellular environment through the pores. For a given cell size, geometry, and orientation, the number of electropores—and their sizecreated in the cell by the applied electric field pulses depends on both the amplitude E of the electric field pulses and the duration t of the pulses. That is, for a given pulse duration t, no pores will be induced in the cell until the amplitude E reaches a certain lower limit. This limit is different for different cells, particularly, for cells of different sizes. The smaller the size of a cell, the higher the electric field required to induce pores and thus the higher the lower limit is. Above the lower amplitude E limit the number of pores and their effective diameter increases proportionally with both increasing field amplitude E and pulse duration t. Electroporation is observed for pulse durations in the range from tens of microseconds to hundreds of milliseconds.

Until the upper limit of electroporation is achieved, an electroporated cell can survive the pulsing and restore its viability thereafter. Above the upper limit the pore diameters and number of induced pores become too large for a cell to survive. The irreversibly chemically imbalanced cell cannot repair itself by any spontaneous or biological process and dies. To kill a cell a potential in the range of 2 to 4 V should be applied along the cell. The cell killing by electroporation is a probabilistic process. That is, increasing the number of applied pulses of duration t leads to an increased probability of cell killing, a probability increase that is approximately equal to the percentage increase in the total time duration of the applied electric pulses.

The survivability of electroporated cells depends significantly on their temperature. At higher temperature cells are more vulnerable to cell death by electroporation. Thus, the amplitude and duration of the electric pulses required for cell killing are lower. It is believed that this observation is explained by two underlying phenomena: at higher temperatures cells are less stable biochemically because of more intense metabolic activity; and, secondly, at elevated temperatures the strength of lipid membranes decreases, which facilitates creating larger pores or irreversible rupture of the cell membrane. At lower temperatures (about 10 to about 20 degrees Celsius) cells are more resistant to electroporation and can survive two to three times higher voltages than they can at body temperature.

The Prostate Gland and Benign Prostatic Hyperplasia

The prostate gland forms part of the male reproductive system. The prostate gland is located between the bladder and the rectum and wraps around the urethra, the tube that carries urine out from the bladder through the penis. The gland consists a dense fibrous capsule enclosing several lobes or regions. The prostate gland is generally composed of smooth muscles and glandular epithelial tissue. The glandular epithelial tissue produces prostatic fluid. The smooth muscles contract during sexual climax and squeeze the prostatic fluid into the urethra as the sperm passes through the ejaculatory ducts and urethra. Prostatic fluid secreted by the prostate gland provides nutrition for ejaculated spermatozoids increasing their mobility and improves the spermatozoids chances for survival after ejaculation by making the environment in the vaginal canal less acidic.

Anatomically, the prostate gland is usually described as including three glandular zones: the central, peripheral and transitional zones. The transitional zone is located right behind the place where the seminal vesicles merge with the urethra. This transitional zone tends to be predisposed to benign enlargement in later life.

The prostate reaches its normal size and weight (about 20 grams) soon after puberty. The size and weight of the prostate typically remain stable until the individual reaches his mid-forties. At this age, the prostate gland—typically in the transitional zone—begins to enlarge through a process of excessive cell proliferation known as benign prostatic hyperplasia (BPH). This overgrowth can occur in both smooth muscle and glandular epithelial tissues and has been attributed to a number of different causes, including hormones and growth factors as well as generally to the aging process.

Benign prostate hyperplasia can cause distressing urination symptoms. As the disease progresses the dense capsule surrounding the enlarging prostate prevents it from further expansion outward and forces the prostate to press against the urethra, partially obstructing the urine flow. The tension in the smooth muscles of the prostate also increases which causes further compression of the urethra and reduction of the urine flow. Some symptoms of BPH stem from the gradual loss of bladder function leading to an incomplete emptying of the bladder. The symptoms can include straining to urinate, a weak or intermittent stream, an increased frequency of urination, pain during urination, and incontinence—the involuntary loss of urine following an uncontrollable sense of urgency. These symptoms alone can negatively affect the quality of life of affected men. Left untreated, BPH can cause even more severe complications, such as urinary tract infection, acute urinary retention, and uremia.

Before age 40, only 10% of men have benign prostatic hyperplasia; but by age 80, about 80% have signs of this condition. Benign prostatic hyperplasia is the most common non-cancerous form of cell growth in men. About 14 million men in US have BPH, and about 375,000 new patients are diagnosed every year.

For many years, researchers have tried to find medications to shrink the prostate or at least stop its growth. Between 1992 and 1997, the FDA approved four drugs for treatment of BPH: finasteride, terazosin, tamsulosin, and doxazosin.

Finasteride inhibits production of hormone DHT. DHT is one of the hormones that have been found to be involved in prostate enlargement. Treatment with Finasteride has been shown to shrink the prostate in some men.

Terazosin, doxazosin, and tamsulosin belong to the class of drugs known as alpha-blockers. Alpha-blockers act by relaxing the smooth muscle of the prostate and bladder to improve urine flow and reduce bladder outlet obstruction. In men with severe symptoms, though, these medications are palliative only. They can delay but not prevent the eventual need for surgery.

Regardless of the efficacy of any drug treatment, the long term exposure to xenobiotic compounds may produce additional unwanted side effects that are not realized until years after treatment. Accordingly, a need exists for an apparatus and method for the treatment of BPH that does not require the introduction of xenobiotic compounds.

For men with the most severe symptoms, surgery is generally considered to be the best long-term solution. There are several surgical procedures that have been developed for relieving symptoms of BPH. Each of these procedures, however, suffers from one or more of the following deficiencies: high morbidity, long hospital stays, the use of general anesthesia, significant side effects such as impotence, and possible complications such as infection and inflammation.

In recent years, a number of procedures have been introduced that are less invasive than surgery. One such procedure is transurethral microwave thermal therapy. In transurethral microwave thermal therapy, a Foley-type catheter containing a microwave antenna is placed within the urethra. The microwave antenna is positioned adjacent to the transitional zone of the prostate, where BPH occurs, and allows selective heating of the prostate. Maintaining the temperature of the BPH tissue above 45 degrees C. during about a one hour session leads to necrosis of the tissues and subsequent reabsorption of necrotic tissue by the body.

Another recently developed non-invasive technique is transurethral needle ablation (TUNA). TUNA uses low level radio frequency (RF) energy to heat the prostate. Using TUNA, two separate needles are inserted into prostate through the urethra. Several watts of RF energy is applied to each needle to cause thermal necrosis of the prostate cells around the needles. Application of this treatment to several sites of the prostate typically results in sufficient necrosis to relieve symptoms of the BPH.

While generally successful, the microwave and RF therapies are relatively long procedures. Also, because of the poor temperature control of the heated volume, the volume of removed tissue is often not sufficient for the long term relief of the symptoms and/or the healthy tissue of the urethra is damaged. A damaged urethra is capable of restoring itself, but the healing is a long morbid process accompanied by sloughing of the necrotic tissue into urethra and excretion of it during urination.

Therefore, a need exists for a minimally invasive therapy for treatment of BPH that requires shorter treatment times and is less morbid than existing therapies.

BRIEF DESCRIPTION OF THE INVENTION

The present invention provides apparatus and methods for the treatment of benign prostate hyperplasia and the alleviation of the symptoms associated therewith. An apparatus in accord with the present invention has a probe portion and a handle portion. The probe portion is preferably entirely or partially hollow.

In an embodiment of the present invention, the probe is a hollow body having proximal, transitional, and distal probe portions. The proximal probe portion is a substantially straight, hollow, elongate tube attached at its proximal end to the handle portion. The proximal probe section is configured to be received within the penile section of the urethra and extend to the urogenital diaphragm, an anatomical structure separating the distal end of the penis from the prostate gland. The distal probe portion is a substantially straight, hollow, elongate tube configured to be received within the prostatic segment of the urethra. The transitional probe portion is a curved, hollow, tube extending between the proximal and distal probe portions to form therewith a continuous, hollow probe capable of being received by the urethra and extending from the penile opening to within the prostate.

The hollow probe portion provides access for a plurality of electrodes and other desirable instrumentation to the prostate gland. For example, a pair of needle electrodes and an flexible fiber optic endoscope can be housed within the probe portion. If desired, separate passages or channels can be provided for the electrodes and the endoscope. The endoscope will preferably extend the length of the probe, from the probe proximal end to the probe distal end. The endoscope may be provided to enable the visualization of the urethra distally to the probe to enable safe placement and manipulation of the inventive apparatus during therapy procedures.

The needle electrodes are slidably disposed within the probe to enable their extension and retraction relative to the probe and into and out of the BPH tissue. The aforementioned channels or passages will facilitate their extension and retraction. In their retracted position, the distal ends of the needles will be positioned within and near or at the distal end of the proximal probe portion. When the probe is properly positioned relative to the prostate gland, advancing the needles will advance them into the BPH tissue of the prostate gland. Only the distal needle ends should be exposed; that is, the proximal portions of the needle electrodes should be insulated to insulate the needle electrodes from the probe body as well as each other. The proximal ends of the needles may be secured to a finger activated lever forming part of the handle portion. The lever is positioned and adapted to advance the needles relative to the probe to pierce the urethra and thus position them in the body of the prostate gland; more specifically, advancing the needles during a procedure will result in the placement of the uninsulated needle ends being disposed substantially within the transition zone where BPH occurs.

The curved probe portion serves to displace the proximal and distal portions from each other. In turn, this displacement displaces the prostatic urethral segment and the penile urethral segments from each other. The electrode needles can thus be advanced substantially parallel to the longitudinal axis of the proximal portion, and thus the penile urethral segment, into the prostate gland. Thus, this displacement facilitates ready and proper positioning of the needle electrodes into the prostate gland without the necessity of bending needles about 90 into the prostate gland and without the associated complicated structures found in the prior art. This probe geometry enables the needles to be placed into the prostate gland substantially parallel to the urethra, which in turn enables the use of fewer treatment positions and shorter treatments.

Preferably, the entirety of the inventive apparatus, save that portion of the distal probe portion that will be disposed within the prostatic urethra, is covered with a insulating biocompatible material. That uninsulated distal probe portion may serve as a third, urethral electrode. All of the electrodes will be electrically insulated from each other and will be electrically connected to a generator producing the electroporation pulses. The amplitude and duration of the pulses will be selected to provide and electric field in the prostatic tissue that exceeds the upper electroporation limit of the BPH fibromuscular and nerve tissues. The duration of the pulses may be selected to range from about 10 microseconds to about 500 milliseconds. As stated, the amplitude, duration, and number of pulses will be preselected to cause necrosis of the fibromuscular and nerve cells constituting the benign prostatic hyperplasia tissues.

In another embodiment of the present invention, the entire probe will be insulated and only the needle electrodes will be utilized for providing electroporation therapy. In this embodiment, no electric pulses will be applied to the probe itself. It is anticipated that this embodiment of the present invention will be used for cases of moderate enlargement of the prostate gland.

Stated alternatively, according to one aspect of the present invention, the probe portion may have at least three sections, wherein the first and third sections take on a substantially tubular form with differing sizes, each of the first and third sections defining a substantially longitudinal axis, with the first and third sections' longitudinal axes lying parallel but not coaxial, and the second section is a transition section between the first and third sections. The third section is desirably sized to be safely, comfortably, and appropriately received within the prostatic segment of the urethra. The first section is desirably sized to be safely, comfortably, and appropriately configured to be received within the urethra and extend from urethral opening through the penis approximately to the urogenital diaphragm. The second or transitional section is desirably sized to be safely, comfortably, and appropriately extend through the urogenital diaphragm. The probe can be manufactured as integral unit or in separate sections that are joined using known manufacturing processes.

In another aspect of the present invention, the first and third probe sections each define a longitudinal axis, with the two axes being non-parallel.

In yet another aspect of the present invention, the needle electrodes may be curved.

In still yet another aspect of the present invention, the needle electrodes may be bent in one location.

In a method in accord with the present invention, a probe having at least first and second probe portions, with the first and second probe portions each defining an axis and the first and second probe portion axes not being collinear, is inserted into the urethra and maneuvered until the distal end of the probe lies within the prostatic urethral segment. The distal or second probe portion displaces the prostate gland sideways relative to the axis of the proximal or first probe portion. Needle electrodes electrically connected to a power source are extended from the first probe portion and inserted into the BPH tissue of the prostate. Electric field pulses of selected amplitude and duration are applied to the BPH tissue. In a preferred embodiment, the electric field is directed radially and thus along the longer dimension of the fibromuscular cells forming benign prostate hyperplasia as well as the nerve cells contained therein.

The present invention, while described below with respect to electroporation, can also be utilized with radio frequency energies alone or in conjunction with electroporation.

The present invention, as well as its various features and advantages, will become evident to those skilled in the art when the following description of the invention is read in conjunction with the accompanying drawings as briefly described below and the appended claims. Throughout the drawings, like numerals refer to similar or identical parts.

DETAILED DESCRIPTION OF THE INVENTION

Figures 1, 2, 3:
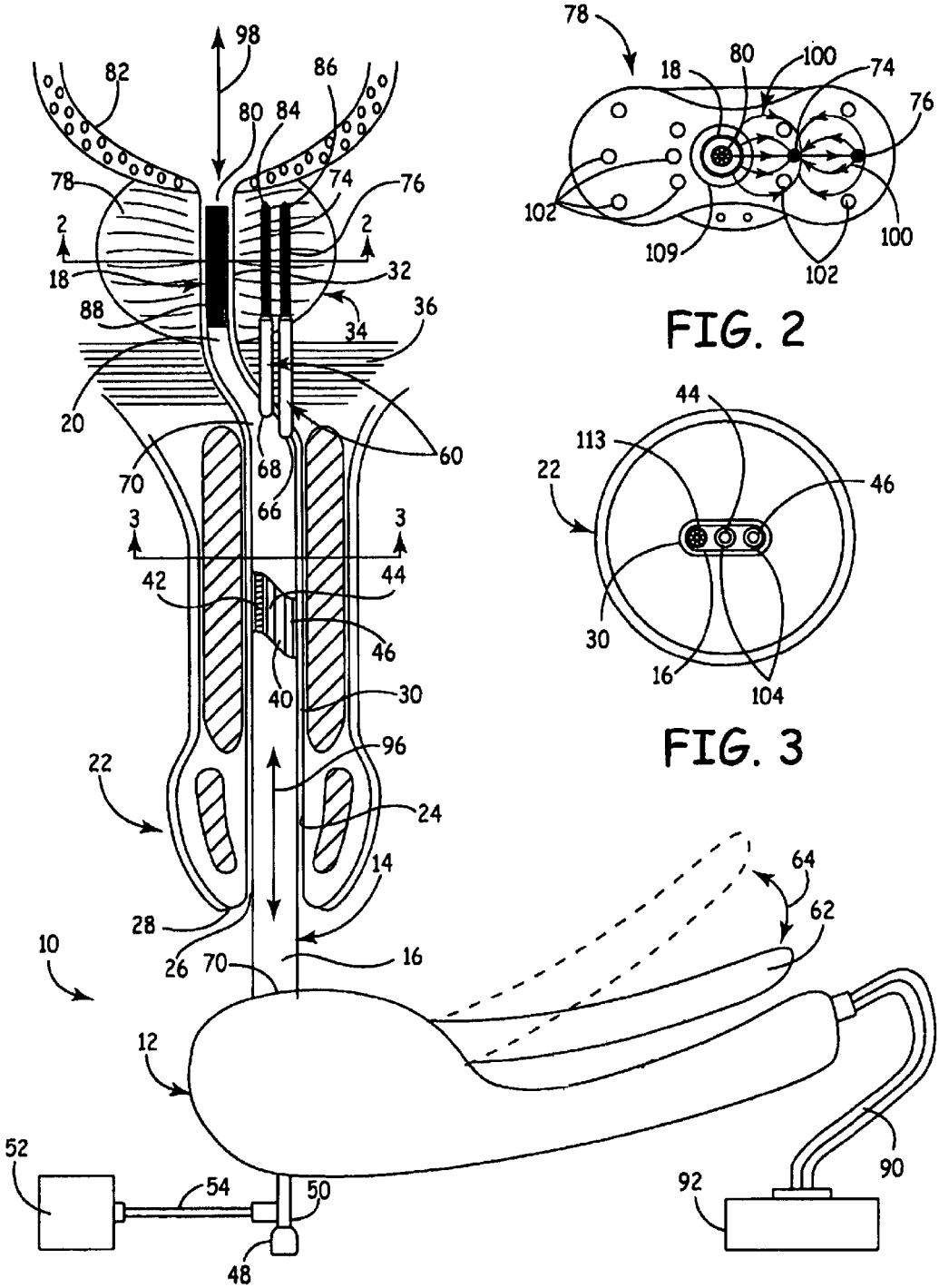
FIG. 1 illustrates an embodiment of the present invention in a partial cross sectional view disposed in an operating position within a human penis and prostate gland.
FIG. 2 shows a cross-sectional view of the present invention taken along viewing plane 2—2 of FIG. 1.
FIG. 3 shows a cross-sectional view of the present invention taken along viewing plane 3—3 of FIG. 1.

Cells are not, generally speaking, spherical bodies. Rather, they come in a variety of sizes and geometries. For example, for cells similar to muscle fiber cells the length to width ratio of the cell can be as great as 20–30 to 1. Nerve cells can have even greater length to width ratios. Cell vulnerability to electroporation, as noted earlier, is different for different directions of the applied electric field. That vulnerability depends on the size of the cell in the direction of the applied field. Thus, the effect of electroporation on tissue can be modulated by selecting a field direction relative to a cell's geometry. Stated otherwise, an elongated cell can be killed with significantly lower electric field strength if the field is applied along the cell. If the field is applied across such a cell, the cell is capable of surviving much higher amplitudes of the electric field.

The current invention provides relief of the symptoms of BPH by providing electroporation treatment to the BPH treatment to create a necrotic zone in the BPH tissue around the urethra. Control of the volume of the necrotic zone, its shape, and its location relative to healthy prostate tissue is provided by the present invention, including a system of electrodes that generate an electric field in the area of benign enlargement of the prostate gland. Application of multiple pulses of the electric field having the appropriate voltage and duration leads to necrosis of the prostatic tissue around the urethra.

Anatomically, the predominant direction of fibers in the fibro-muscular glandular tissue of BPH is radial to the urethra. In the present invention, the preferred direction of the applied electric field is also radial to the urethra, coinciding with the predominant direction of the BPH tissue. Application of the electroporating pulses along the muscular fibers and nerves that anatomically follow them selectively kills both types of fibers. Thus, two intermediate benefits of the present therapy are achieved with selective application of electroporation pulses to BPH tissue. First, a significant volume of necrotic BPH tissue around the urethra is created by the therapy. Second, the nerves that cause elevation in tension of the muscle fibers are destroyed. Subsequently, the necrotic tissue, including both the killed BPH tissue and nerves, are removed by macrophages. Removal of the necrotic BPH tissue reduces the total volume of BPH and pressure on the urethra while removal of the destroyed nerves results in relaxation of the prostate. Both effects contribute to the improvement of the urethra and bladder functions after treatment.

While the aforementioned therapy alleviates the symptoms of BPH, care must be taken to avoid damaging or destroying other tissue in the vicinity of the applied electroporation pulses. For example, sphincters, located on the urethra anterior and posterior to the prostate gland, consist of smooth muscle cells wrapped circumferentially around the urethra. These urethral sphincters control shutting down the flow of urine from the bladder and should be preserved during a therapy treatment. An electroporation field applied radially to the prostate—that is, coincident with the elongate fibromuscular and nerve cells of the BPH—results in the field being transverse to the sphincter muscle cells, thus making them relatively resistant to the electroporation pulsing. Thus, by selectively directing the electric field, damage to these muscles, whose health and function are important to quality of life for affected individuals, can be reduced or avoided. Nevertheless, to reduce the potential of damage to the sphincter muscles further, the electrodes disposed within the urethra during therapy should not be positioned too closely to them. Additionally, the amplitude of the electric field during treatment applied to the urethra area should be selected not to exceed the upper electroporation limit of the sphincter muscles in the transverse direction.

The foregoing therapeutic benefits are obtained by providing electroporation treatment to BPH by apparatus and methods in accord with the present invention.

A BPH therapy applicator and methods of providing BPT treatment in accord with the present invention are described below with reference to FIGS. 1–3. Referring specifically to FIG. 1, this Figure illustrates a BPH therapy applicator 10 comprising a handle 12 and a probe 14. Probe 14 includes at least first and second, or proximal and distal sections, 16 and 18, respectively. In the embodiment shown, probe 14 also includes a third or transitional section 20. The applicator 10 is shown relative to a penis 22 in position for the application of an electroporation treatment to a patient experiencing BPH. Thus, the probe 10 is shown inserted into the urethra 24 through the urethral opening 26 at the proximal end of the penis 22. As shown in its operational position, probe proximal portion 16 is disposed within the penile urethral segment 30, probe distal portion 18 is disposed within the prostatic urethral segment 32, and probe transitional portion 20 extends between the proximal and distal probe portions 16 and 18 and is disposed substantially through the urogenital diaphragm 34.

Probe 14 has a substantially hollow configuration, to provide an interior passage 40. Passage 40 provides access for a flexible fiber optic endoscope 42 and at least one needle 44. In the embodiment shown in FIG. 1, two needles, 44 and 46, are shown. One or more of the endoscope 42 and needles 44 and 46 may be enclosed within their own individual channels if desired. The endoscope 42 extends to an eye piece 48 at its proximal end 50. A light source 52, which is connected to the endoscope 42 by a fiber optic cable 54, enables visualization of the urethra during placement and manipulation of the applicator 10 in operation position and during a BPH electroporation treatment.

Needles 44 and 46 have insulating sheathes 60 on their surfaces that electrically separate or isolate them from the handle 12 and probe 14 as well as each other. Needles 44 and 46 are attached to a finger-activated lever 62 at their proximal ends in any known, appropriate manner. As seen in the Figure, lever 62 has been moved from its non-operational position seen in phantom to an operational position as indicated by the double-headed arrow 64. Movement of the lever 62 between the two positions will cause the needles to extend from their non-operational position to an operational position as seen in the Figure and to retract into their non-operational position as desired by the lever operator. Thus, movement of the lever to the operational position shown will cause the needles to extend or advance through holes 66 and 68 in the distal end 70 of the first or proximal probe section 16. The advancement of the needles 66 and 68 out of the probe 14 causes the needles to pierce the urethra 24 and the urogenital diaphragm 36 and disposes the uninsulated needle ends 74 and 76 of needles 44 and 46, respectively, which form a pair of electrodes, in the body of the prostate gland 78. Preferably, both the lengths and the operating positions of the distal end of the distal end 80 of the probe 14 and the needle electrodes 44 and 46 are selected to avoid reaching the bladder 82 to reduce the likelihood of damage thereto during a procedure. In particular, the sharp tips 84 and 86 of needles 44 and 46, respectively, should not penetrate the bladder 82.

The entirety of the surface of the applicator 10, save for a small portion 88 of the distal probe section 18 is covered with an insulating, biocompatible layer of any known or hereafter discovered, appropriate material. Uninsulated distal probe section portion 88 is therefore exposed to the surrounding tissue and can comprise a third, urethral electrode of the applicator 10. Electrodes 74, 76, and 88 are electrically insulated from each other and are connected via an appropriate connector 90 to a generator 92 that produces high voltage electrical pulses. As noted previously, the amplitude and duration of the electric pulses applied between the electrodes will be selected to provide an electric field in the prostatic tissue exceeding the upper electroporation limit of the BPH tissue, including the nerve cells contained therein. The pulse duration may be selected to be within the range of about 10 microseconds to about 500 milliseconds. The amplitude and number of applied pulses are selected to cause necrosis of the BPH tissue, including the nerves and muscle cells.

It will be observed that the proximal and distal probe sections 16 and 18 define longitudinal axes 96 and 98 respectively. As shown, axes 96 and 98 are not co-linear. They may, if desired, lie parallel to each other, however. Proximal section 16 has a larger cross-sectional area than the distal section 18, which does not need to carry the needles 44 and 46 therein, thus aiding to increase patient comfort during a procedure. Probe section 20 transitions between the larger cross-sectional area proximal section 16 and smaller cross-sectional area section 18. Additionally, the angled or curved nature of the section 20 serves to offset the proximal and distal sections 16 and 18, respectively, from each other. In doing so, the prostate gland 78 is displaced sideways relative to the axis 96 of the proximal section 16. This sideways displacement facilitates proper positioning of the needle electrodes in the BPH tissue.

Referring now specifically to FIG. 2, a cross-section of the prostate gland 78 is shown taken along viewing plane 2—2 of FIG. 1 with the applicator 10 in its operating position. When electric pulses are applied between the urethral electrode 88 and needle electrodes 74 and 79, the electric field generated between the electrodes, indicated generally by field lines 100, causes necrosis of the BPH tissue. After an electroporation treatment in one site of the prostate gland is completed, the needles can be retracted within probe 14 and the probe can be rotated a selected angle to a new position for treatment. The needles will be advanced into the operating position and the electric pulses applied once again. A plurality of such needle advancements and treatments are indicated in the Figure by the open circles 102.

Referring now specifically to FIG. 3, a cross-section of the prostate gland 78 is shown taken along viewing plane 3—3 of FIG. 1 with the applicator 10 in its operating position. As shown, the proximal probe section 16 preferably has a substantially elliptical configuration with a ratio of the axes in the range of about 1:3 to about 1:4. The maximal diameter of the ellipse should generally not exceed about 12 to about 16 mm and minimal diameter should generally not be less than about 3 to about 4 mm. The fiber bundle 42 of the endoscope and the tow needles 44 and 46 are positioned in line along the longer axis of the probe section 16. As seen in the Figure, needles 44 and 46 are disposed, if desired, within channels or tubes 104.

Figure 4:
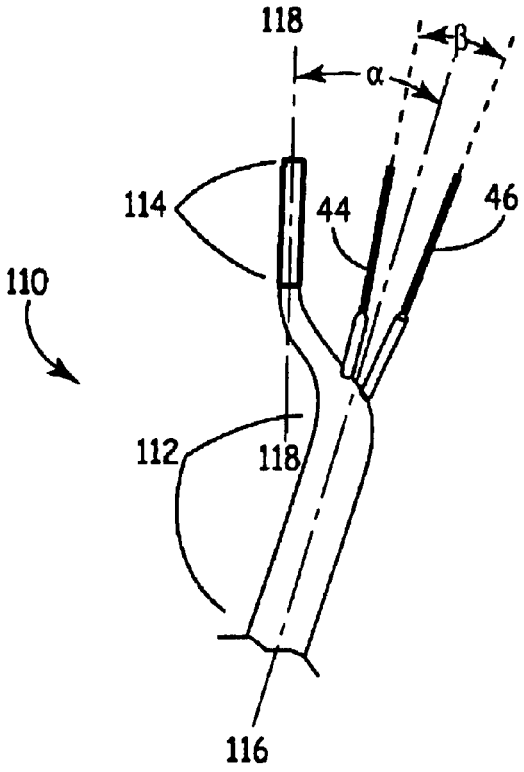
FIG. 4 depicts an alternative embodiment of an apparatus in accord with the present invention.
Figure 5:
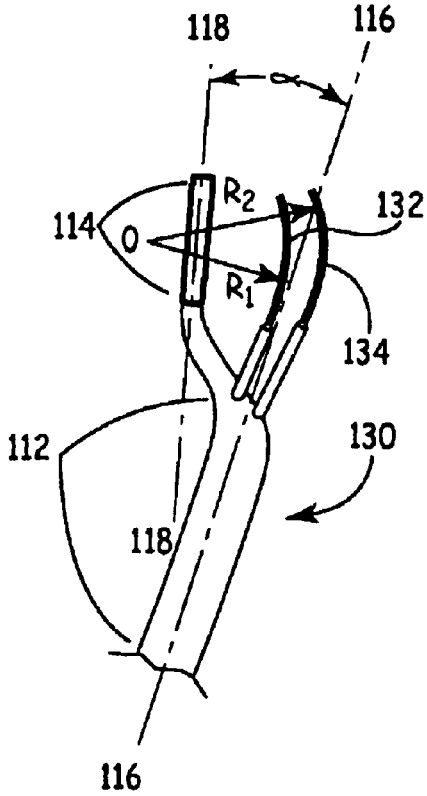
FIG. 5 illustrates an alternative embodiment of an apparatus in accord with the present invention.
Figure 6:
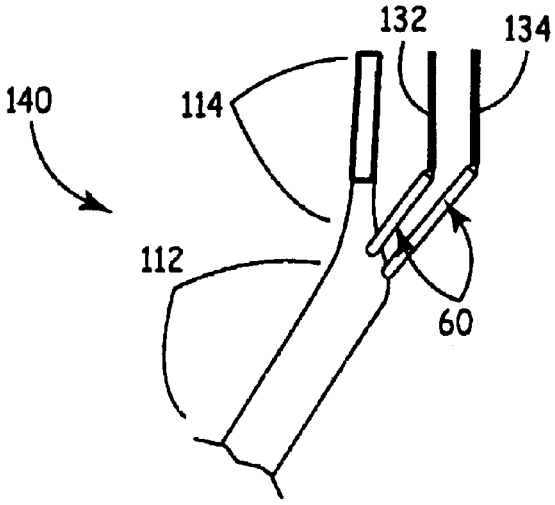
FIG. 6 shows an alternative embodiment of an apparatus in accord with the present invention.

FIGS. 4–6 show alternative embodiments of the present invention. In FIG. 4, probe 110 includes proximal and distal segments 112 and 114, respectively. Segments 112 and 114 each define an axis 116 and 118, respectively. As indicated, axes 116 and 118 do not lie parallel to each other, but are separated by an angle a lying in the range of about 10° to about 45°. Also as shown, the needles 44 and 46 can, if desired, be angularly disposed relative to each other. As seen in the Figure, needles 44 and 46 diverge by an angle β lying in the range of about 0° to about 30°. In this embodiment, the proximal segment 112 can be made smaller, thus increasing patient comfort.

FIG. 5 illustrates an embodiment 130 of the present invention wherein curved needles 132 and 134 having radii of curvature $R_1$ and $R_2$, respectively, are used rather than the straight needles 44 and 46 previously illustrated and discussed. Where such curved needles are utilized, the radius of curvature of the needles are in the range of about 2 cm to about 5 cm.

FIG. 6 depicts another embodiment of the present invention. In this embodiment, probe 140 includes needles 142 and 142 that are bent at one location; as shown, the needles 142 and 144 are bent at the end of the insulating sheath 60.

Operatively, the probe of the present invention will be introduced into a patient's urethra under endoscopic guidance until the distal end is positioned in the prostatic segment of the patient's urethra. The needle electrodes will then be advanced into the BPH tissue surrounding the urethra and a plurality of electric pulses will be applied. The electroporation therapy will terminate when a significant and stable drop in the electrical resistance of the treated tissue occurs. The resistance drop indicates a profound electroporation damage to the fibromuscular cells, which later leads to their necrosis and dissolution by macrophages. Overall treatment of one site may take about ten pulses and several seconds to several tens of seconds in time depending on the repetition rate of the high voltage pulse generator. After each treatment the needle electrodes will be withdrawn and repositioned in another treatment site. Consecutive treatments are performed in light of patient comfort and safety and until the operator determines that a sufficient volume of BPH tissue has been treated.

It will be obvious to those skilled in the art that many modifications may be made within the scope of the present invention without departing from the spirit of thereof, and the invention includes all such modifications.

What is claimed is:

1. An apparatus for providing electroporation therapy for benign prostatic hyperplasia, said apparatus comprising:

a urethral applicator configured for insertion into a urethra, said applicator including:

a substantially hollow probe, said probe portion including first, second and third probe portions, said first probe portion being configured for insertion into the penile urethral segment and said third probe portion being configured for insertion into the prostatic urethral segment, said first and third probe portions defining first and second probe portion longitudinal axes, wherein said axes are not collinear with each other and wherein said second probe portion lies between said first and third probe portion;

a handle, said handle being attached to said probe;

a plurality of needle electrodes, said electrodes being mounted within said first probe portion for reciprocal movement into and out of said first probe portion substantially parallel to the urethra, said electrodes being provided for connection to an electric pulse generator;

wherein when said applicator is disposed in operating position, said needle electrodes may be advanced into benign prostatic hyperplasia tissue for electroporation therapy.

2. The apparatus of claim 1 wherein said first and second probe portion longitudinal axes are parallel.

3. The apparatus of claim 1 wherein said first and second probe portion longitudinal axes are non-parallel.

4. The apparatus of claim 1 wherein said third probe portion is uninsulated and is provided for electrical connection to a pulse generator.

5. The apparatus of claim 1 wherein said first probe portion has a greater cross-sectional area than said third probe portion.

6. The apparatus of claim 1 wherein said needle electrodes are curved.

7. The apparatus of claim 1 wherein said needle electrodes are bent.

8. The apparatus of claim 1 and further including a flexible fiber optic endoscope.

9. The apparatus of claim 1 and further including an electric pulse generator.

10. The apparatus of claim 9 wherein said third probe portion is uninsulated and is electrically connected to a said electric pulse generator.

11. The apparatus of claim 1 wherein said first and third probe portions are longitudinally offset relative to each other.

12. The apparatus of claim 1 wherein said first and third probe portions are angularly off-set relative to each other.

13. The apparatus of claim 1 wherein said needle electrodes are electrically insulated from each other and said applicator.

14. The apparatus of claim 1 wherein said handle includes a lever engaged with said needle electrodes to enable the operator to selectively advance and retract said needle electrodes.

15. A method of providing electroporation therapy for benign prostatic hyperplasia comprising:

providing an applicator including a probe having a proximal probe portion and a distal probe electrode portion, said portions each defining non-collinear longitudinal axes, said probe including at least one electrode for electroporation therapy;

inserting the applicator into a patient's urethra to dispose the distal probe portion in the prostatic urethral segment and the proximal probe portion in the penile urethral segment and to displace the patient's prostate gland sideways relative to the proximal probe portion;

advancing at least a first electrode into the benign prostatic hyperplasia tissue; and applying electric pulses to the distal probe electrode portion and the at least first electrode to generate electroporating electric fields.

16. The method of claim 15 and further including:

retracting the at least first electrode following the completion of electroporation therapy at a first site rotating the probe a preselected amount;

advancing the at least first electrode into the benign prostatic hyperplasia tissue at a new location in the tissue; and applying electric pulses to the distal probe electrode portion and the at least first electrode to generate electroporating electric fields.

* * * * *